United States Patent
Lee et al.

(10) Patent No.: US 8,350,243 B2
(45) Date of Patent: Jan. 8, 2013

(54) OPTICALLY INDUCED DIELECTROPHORESIS CHIP FOR CONTROL AND ANALYSIS OF BIO-MOLECULES

(75) Inventors: Gwo-Bin Lee, Tainan (TW);
Tzung-Fang Guo, Chiayi County (TW);
Wei Wang, Taipei (TW); Yen-Heng Lin, Taoyuan County (TW)

(73) Assignee: National Cheng Kung University, Tainan (TW)

( * ) Notice: Subject to any disclaimer, the term of this patent is extended or adjusted under 35 U.S.C. 154(b) by 394 days.

(21) Appl. No.: 12/461,899

(22) Filed: Aug. 27, 2009

(65) Prior Publication Data
US 2010/0051465 A1 Mar. 4, 2010

(30) Foreign Application Priority Data

Aug. 28, 2008 (TW) .............................. 97132878 A

(51) Int. Cl.
*G01N 21/86* (2006.01)
*G01V 8/00* (2006.01)

(52) U.S. Cl. ................ 250/559.04; 250/208.1; 204/451; 204/601; 204/643

(58) Field of Classification Search .................. 250/551, 250/208.1, 559.04; 430/58.05, 60, 58.7, 430/70, 159, 57.5; 204/643, 451, 601, 412, 204/603
See application file for complete search history.

(56) References Cited

U.S. PATENT DOCUMENTS

| 7,009,190 | B1 * | 3/2006 | Stephenson et al. ...... 250/504 R |
| 7,612,355 | B2 * | 11/2009 | Wu et al. .................. 250/559.04 |
| 2007/0053046 | A1 * | 3/2007 | Tench et al. .................... 359/237 |
| 2007/0095669 | A1 * | 5/2007 | Lau et al. ....................... 204/547 |
| 2007/0290287 | A1 * | 12/2007 | Freedman ..................... 257/443 |

OTHER PUBLICATIONS

Wang et al., "Bulk-heterojunction polymers in optically-induced dielectrophoretic devices for the manipulation of microparticles", Optics Express, vol. 17, No. 20, Sep. 28, 2009, pp. 17603-17613.*
J. Shimada, "Development of Micro-particle DEP Tweezers," Department of Aeronautics and Astronautics, National Cheng Kung University, Master Thesis, Jun. 1995 (pp. 13-14, 25-26, Figure 3.3, and Abstract).
Gang Li et al., "High-efficiency solution processable polymer photovoltaic cells by self-organization of polymer blends," Nature Materials, 2005, vol. 4, pp. 864-868.
F. Padinger et al., "Effects of Postproduction Treatment on Plastic Solar Cells," Advanced Functional Materials, Jan. 2003, vol. 13, Issue 1, pp. 85-88.

* cited by examiner

*Primary Examiner* — Francis M Legasse, Jr.
(74) *Attorney, Agent, or Firm* — Jacobson Holman PLLC

(57) ABSTRACT

An optically-induced dielectrophoresis chip including a substrate, a first electrode layer disposed on the substrate, and an interface modification layer disposed on the first electrode layer. A photo-conductive layer is disposed on the interface modification layer and includes an optical absorbent polymeric material. A barrier layer is disposed on the photo-conductive layer, and a compartment forming layer is disposed on the barrier layer defining a compartment. A second electrode layer covers the compartment forming layer.

9 Claims, 4 Drawing Sheets

OPTICALLY INDUCED DIELECTROPHORESIS CHIP FOR CONTROL AND ANALYSIS OF BIO-MOLECULES

CROSS-REFERENCE TO RELATED APPLICATION

This application claims priority of Taiwanese Application No. 097132878, filed on Aug. 28, 2008.

BACKGROUND OF THE INVENTION

1. Field of the Invention

The invention relates to an optically-induced dielectrophoresis chip, more particularly to an optically-induced dielectrophoresis chip for controlling and analyzing bio-molecules.

2. Description of the Related Art

Technologies for controlling and analyzing bio-molecules are used extensively. One of the technologies is optically-induced dielectrophoresis, which is conducted by projecting an optical pattern on an optical absorbent chip using an optical projecting device so as to produce optically-induced dielectrophoretic force, which causes the bio-molecules to be mobilized. The optically-induced dielectrophoresis simplifies the pretreatment procedure for a bio-sample.

However, a photo-conductive layer of the chip is made of amorphous silicon. The amorphous silicon photo-conductive layer is made by a semiconductor procedure which is conducted using a plasma-enhanced chemical vapor deposition system at an elevated temperature above 250° C. Therefore, the production of the conventional chip is complicated and costly.

SUMMARY OF THE INVENTION

Therefore, an object of the present invention is to provide an optically-induced dielectrophoresis chip which can be produced through a cost-reduced and simple process.

Accordingly, the optically-induced dielectrophoresis chip of this invention includes a substrate, a first electrode layer disposed on the substrate, an interface modification layer disposed on the first electrode layer, a photo-conductive layer disposed on the interface modification layer and including an optical absorbent polymeric material, a barrier layer disposed on the photo-conductive layer, a compartment forming layer disposed on the barrier layer and defining a compartment, and a second electrode layer covering the compartment forming layer.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
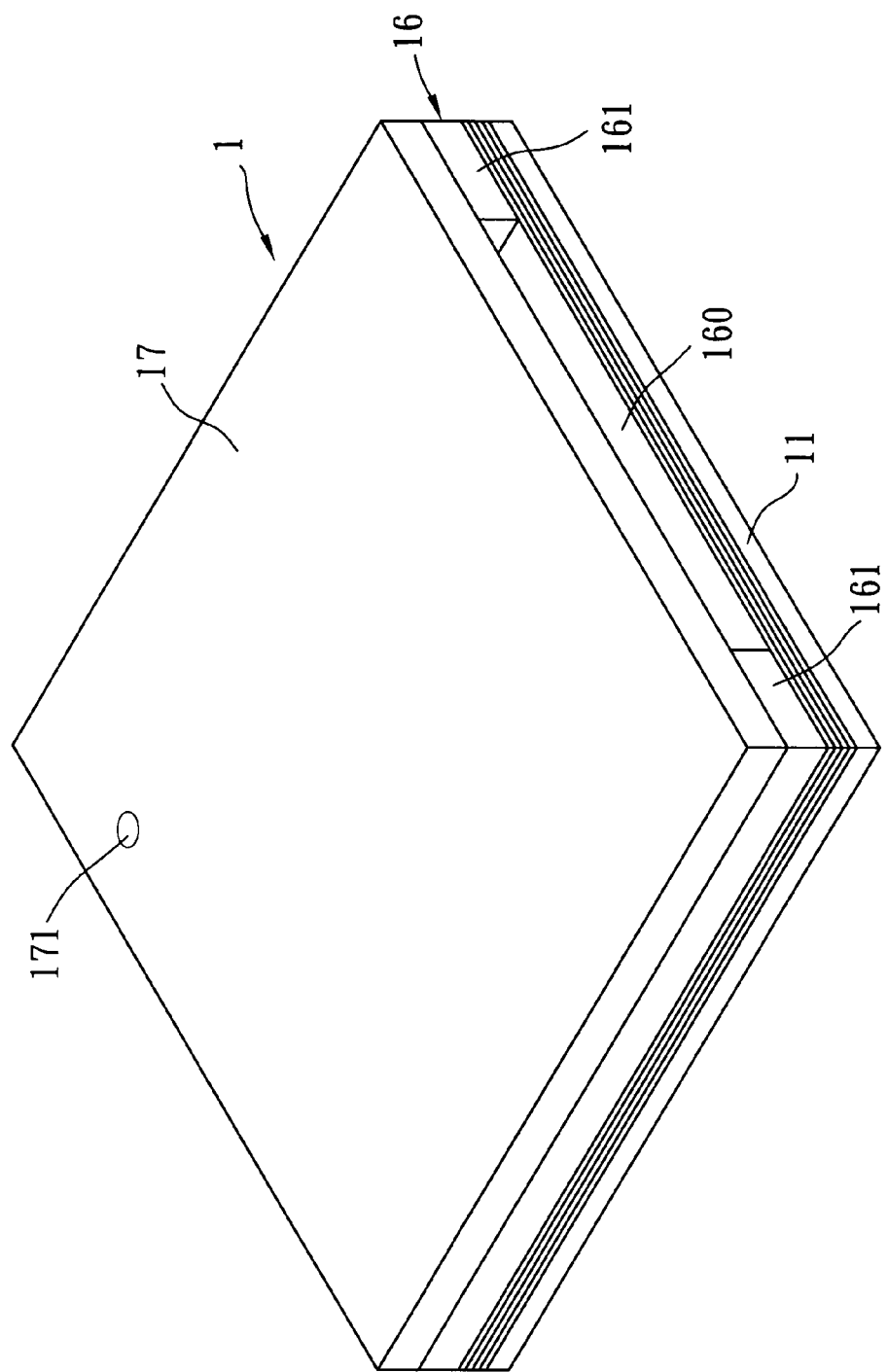
FIG. 1 is a perspective view of a preferred embodiment of an optically-induced dielectrophoresis chip according to this invention.
Figure 2:
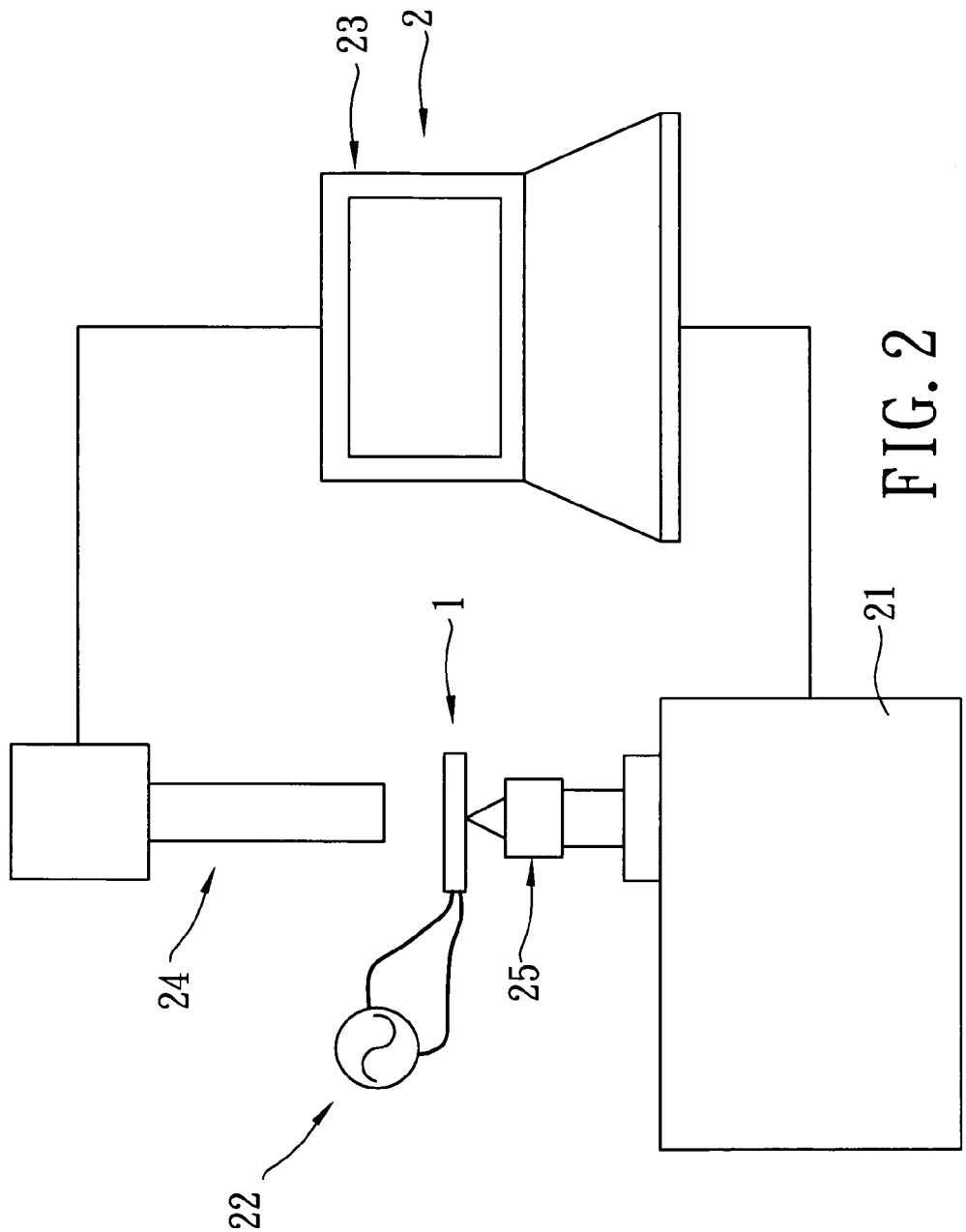
FIG. 2 is a schematic diagram illustrating the use of the preferred embodiment in a control system.
Figure 3:
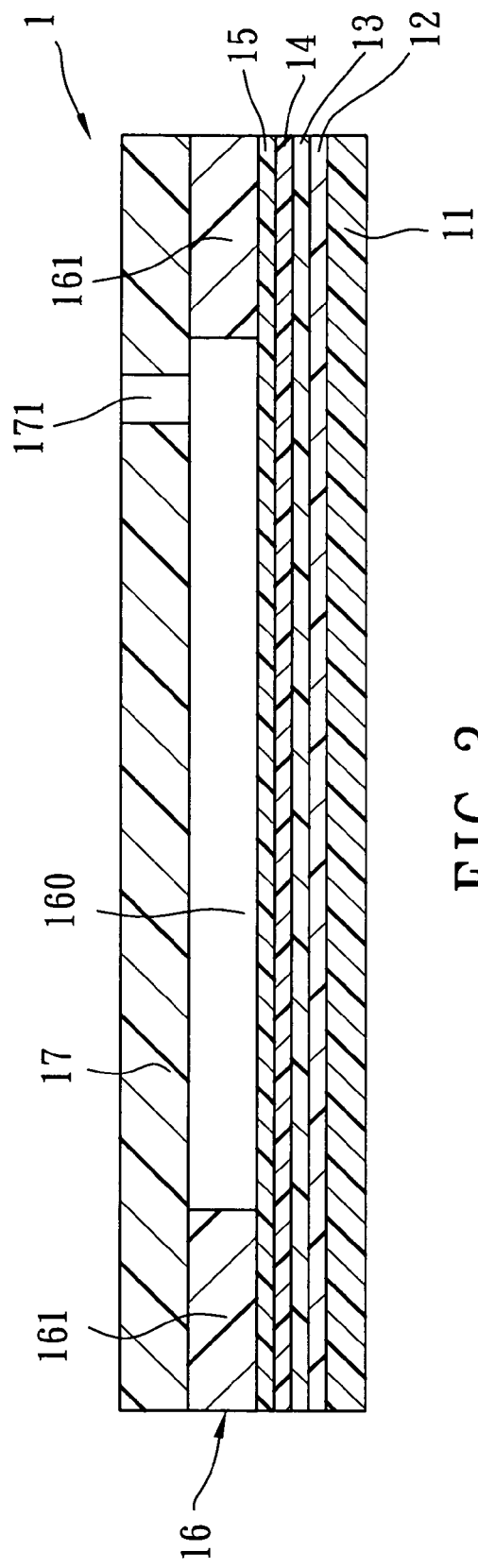
FIG. 3 is a sectional view of the preferred embodiment.
Figure 4:
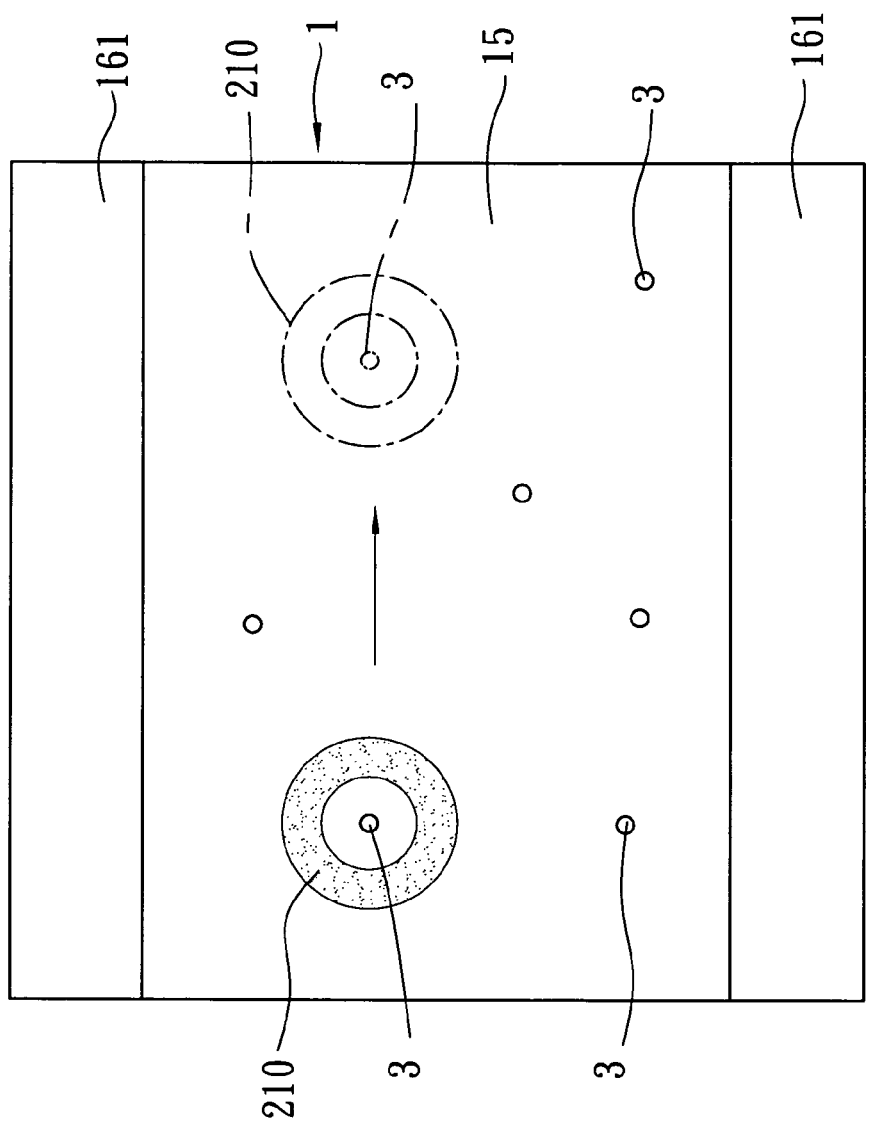
FIG. 4 is a schematic view illustrating the operation of the preferred embodiment.

Referring to FIGS. 1 to 4, the preferred embodiment of an optically-induced dielectrophoresis chip 1 according to this invention is used along with a control system 2 so as to produce optically-induced dielectrophoresis for controlling the motion of a bio-molecule 3. The control system 2 includes a projecting device 21 for projecting light toward the optically-induced dielectrophoresis chip 1, a power supplying device 22 for supplying alternating current power to the optically-induced dielectrophoresis chip 1, a pattern-controlling device 23 for controlling a pattern of the light projected by the projecting device 21, and an image pick-up device 24 for capturing a motion image of the bio-molecule 3. The projecting device 21 is, for example, a digital light processing projector or an LCD projector. The pattern-controlling device 23 is, for example, a computer.

The optically-induced dielectrophoresis chip 1 includes a substrate 11, a first electrode layer 12 disposed on the substrate 11, an interface modification layer 13 disposed on the first electrode layer 12, a photo-conductive layer 14 disposed on the interface modification layer 13, a barrier layer 15 disposed on the photo-conductive layer 14, a compartment forming layer 16 disposed on the barrier layer 15, and a second electrode layer 17 covering the compartment forming layer 16.

The substrate 11 is formed as a square plate, and is made of a glass or plastic material. Preferably, the substrate 11 is made of a flexible plastic material.

The first electrode layer 12 is made of indium tin oxide, and is disposed on the substrate 11 by spin coating, vapor depositing, sputtering, or the like.

The interface modification layer 13 is made of an electro-conductive polymeric material. The electro-conductive polymeric material suitable in the preferred embodiment is poly (3,4-ethylenedioxythiophene), poly sodium p-styrene sulfonate, or a mixture thereof. Preferably, the electro-conductive polymeric material is a mixture of poly (3,4-ethylenedioxythiophene) and poly sodium p-styrene sulfonate in a weight ratio of 1:6. The interface modification layer 13 is used for modifying the evenness of the first electrode layer 12.

The photo-conductive layer 14 is made of an optical absorbent polymeric material. The optical absorbent polymeric material suitable in the preferred embodiment is poly (3-hexylthiophene), [6,6]-phenyl C61 butyric acid methyl ester, or a mixture thereof. Preferably, the optical absorbent polymeric material is a mixture of poly (3-hexylthiophene) and [6,6]-phenyl C61 butyric acid methyl ester in a weight ratio of 1:1. The photo-conductive layer 14 is formed by spin coating the optical absorbent polymeric material on the interface modification layer 13 under a nitrogen atmosphere. Preferably, the photo-conductive layer 14 has a thickness ranging from 300 nm to 500 nm. When the thickness of the photo-conductive layer 14 is less than 300 nm, the optically-induced dielectrophoresis may be unsatisfactory. When the photo-conductive layer 14 is more than 500 nm, the surface thereof may be uneven.

Since the polymeric material has superior optical absorbency and photoelectric conversion efficiency, the electrons and holes in the polymeric material can be separated effectively to destroy the equilibrium of electric field and to facilitate the generation of dielectrophoresis.

In this embodiment, the barrier layer 15 is made of lithium fluoride and is formed by vapor depositing. The barrier layer 15 can isolate steam and oxygen contained in air from the photo-conductive layer 14 and the interface modification layer 13.

The compartment forming layer 16 is composed of two segments 161 spaced apart from each other to define a compartment 160 for a solution containing bio-molecules 3 to flow therein. In this embodiment, the compartment 160 has two opposite openings. Alternatively, the compartment forming layer 16 can be formed as a U-shaped configuration so as to define a compartment having an opening. The compartment forming layer 16 in this preferred embodiment is formed using double-sided adhesive tape available from Adhesives Research.

The second electrode layer 17 is made of indium tin oxide, and includes a through hole 171 communicated with the compartment 160 of the compartment forming layer 16.

In use, the solution containing bio-molecules 3 or the other particles to be operated is poured into the compartment 160 of the compartment forming layer 16 via the through hole 171 in the second electrode layer 17. In this embodiment, polystyrene beads are used to simulate the bio-molecules 3. The first and second electrode layers 12, 17 are electrically connected to the power supplying device 22, and are supplied with alternating current power. The pattern-controlling device 23 controls the projecting device 21 to project a predetermined photo pattern 210 to the optically-induced dielectrophoresis chip 1 via a lens device 25. In this preferred embodiment, the photo pattern 210 is circular.

The area of the photo-conductive layer 14 corresponding to the photo pattern 210 produces a non-uniform electric field to exert a dielectrophoretic force on the bio-molecules 3 and to limit the bio-molecules 3 within the area confined by the photo pattern 210. When the position of the photo pattern 210 projected to the optically-induced dielectrophoresis chip 1 is changed, the bio-molecules 3 can be moved along with the photo pattern 210 by the dielectrophoretic force.

As described above, since the polymeric material used as the photo-conductive layer 14 has superior optical absorbency and photoelectric conversion efficiency, the generation of dielectrophoresis can be facilitated. Furthermore, since the polymeric material is flexible, it can be deposited on a flexible substrate (such as a flexible plastic substrate).

Additionally, the conventional chip containing an amorphous silicon photo-conductive layer is usually made at an elevated temperature of at least 250° C. Contrary to the prior art, the optically-induced dielectrophoresis chip 1 of the present invention can be made at a temperature of no more than 40° C., and thus can be produced in a cost-reduced and simple manner. Since the cost for production of the conventional chip is relatively high, the conventional chip is usually reused. Therefore, a time-consuming washing procedure is required prior to reuse of the conventional chip. Oppositely, since the optically-induced dielectrophoresis chip 1 of the present invention can be made in a cost-reduced and simple manner, it can be discarded after use.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

We claim:

1. An optically-induced dielectrophoresis chip, comprising:
    a substrate;
    a first electrode layer disposed on said substrate;
    an interface modification layer disposed on said first electrode layer;
    a photo-conductive layer disposed on said interface modification layer and including an optical absorbent polymeric material;
    a barrier layer disposed on said photo-conductive layer;
    a compartment forming layer disposed on said barrier layer and defining a compartment; and
    a second electrode layer covering said compartment forming layer,
    wherein said optical absorbent polymeric material is selected from the group consisting of poly (3-hexylthiophene) and [6,6]-phenyl C61 butyric acid methyl ester,
    wherein said interface modification layer includes an electro-conductive polymeric material selected from the group consisting of poly (3,4-ethylenedioxythiophene) and poly sodium p-styrene sulfonate, and
    wherein said photo-conductive layer has a thickness ranging from 300 nm to 500 nm.

2. The optically-induced dielectrophoresis chip as claimed in claim 1, wherein said optical absorbent polymeric material is a mixture of poly (3-hexylthiophene) and [6,6]-phenyl C61 butyric acid methyl ester.

3. The optically-induced dielectrophoresis chip as claimed in claim 2, wherein said mixture of poly (3-hexylthiophene) and [6,6]-phenyl C61 butyric acid methyl ester is in a weight ratio of 1:1.

4. The optically-induced dielectrophoresis chip as claimed in claim 1, wherein said electro-conductive polymeric material includes a mixture of poly (3,4-ethylenedioxythiophene) and poly sodium p-styrene sulfonate.

5. The optically-induced dielectrophoresis chip as claimed in claim 1, wherein said substrate is made of a flexible material.

6. The optically-induced dielectrophoresis chip as claimed in claim 1, wherein said barrier layer includes lithium fluoride.

7. The optically-induced dielectrophoresis chip as claimed in claim 1, wherein each of said first and second electrode layer includes indium tin oxide.

8. The optically-induced dielectrophoresis chip as claimed in claim 1, wherein said second electrode layer includes a through hole communicated with said compartment of said compartment forming layer.

9. The optically-induced dielectrophoresis chip as claimed in claim 5, wherein said flexible material includes a plastic material.

* * * * *